United States Patent [19]

Running

[11] Patent Number: 5,792,631
[45] Date of Patent: Aug. 11, 1998

[54] MICROBIAL PROCESS FOR THE PRODUCTION OF ASCORBIC ACID USING *CHLORELLA PROTOTHECOIDES*

[75] Inventor: Jeffrey Running, Manitowoc, Wis.

[73] Assignee: DCV, Inc., Wilmington, Del.

[21] Appl. No.: 484,155

[22] Filed: Jun. 7, 1995

Related U.S. Application Data

[63] Continuation-in-part of Ser. No. 196,338, Feb. 10, 1994, abandoned, and Ser. No. 853,379, Mar. 18, 1992, abandoned, which is a continuation-in-part of Ser. No. 650,886, Feb. 5, 1991, abandoned, which is a continuation of Ser. No. 750,828, Jul. 1, 1985, Pat. No. 5,001,059, said Ser. No. 196,338, is a continuation-in-part of Ser. No. 853,476, Mar. 18, 1992, abandoned, which is a continuation-in-part of Ser. No. 650,886, and Ser. No. 896,724, Jun. 9, 1992, abandoned, which is a continuation of Ser. No. 650,886.

[51] Int. Cl.$^6$ ............... C12P 7/54; C12P 7/60; C12N 1/12
[52] U.S. Cl. ............... 435/137; 435/138; 435/257.3; 435/172.1; 435/946
[58] Field of Search ............... 435/137, 136, 435/138, 257.3, 946, 172.1

[56] References Cited

U.S. PATENT DOCUMENTS 5,001,059  3/1991  Skatrud et al. ............... 435/137

OTHER PUBLICATIONS

"1993 List of UTEX Cultures", Culture Collection of Algae, Department of Botany, University of Texas at Austin, pp. 23–24, (1993).

Aaronson et al., "The Cell Content and Secretion of Water–Soluble Vitamins by Several Freshwater Algae", *Arch. Microbiol* 112: 57–59, (1977).

Ahmad et al., "Growth and Photosynthesis of *Chlorella protothecoides* Under Different Nutritional Conditions", *J. Phycology*, 25, Supp. 2, (1989) (Abstract only).

Albertano et al., "*Chlorella protothecoides* Krüger var. *acidicola*, a new variety from very low pH environments", *Arch. Hydrobiol. Suppl.* 67, 4, pp. 401–408, (Dec. 1984).

Barnett et al., "Quantitative Recovery of Prototheca from the Environment", *Abstracts of the Annual Meeting*, Mm46 p. 143, (1974).

Bayanova and Trubachev, *Prikladnaya Biokhimiya i Microbiologyia* 17: 400–407 (UDC 582. 26: 577.16), (1981).

Becker et al., "Major Results of the Indo–German Algal Project", *Arch Hydrobiol. Beih*, vol. 11, pp. 23–40, (1978).

Casselton et al., "Ammonium Assimilation *Prototheca zopfii* Krüger", *British Phycological Society*, vol. 17, No. 2, pp. 230–231, (1982).

Ciferri, "Spirulina, the Edible Microorganism", *Microbiological Reviews* 47:551–578 (1983).

Considine, "Ascorbic Acid (Vitamin C)" *Van Nostrand's Scientific Encyclopedia*, vol. 1, pp. 237–238, (1989).

Conte, et al., "Taxonomic Implications of Prototheca and Chorella Cell Wall Polysaccharide Characterization", *Arch. Mikrobiol.*, vol. 92 pp. 227–233, (1973).

Douglas et al., "On the Characteristics and Taxonomic Identity of Chlorella in Symbiosis With Invertebrates", *British Phycological Society*, vol. 20, No. 2, p. 184, (1985).

Gruen et al., "Determination of Ascorbic Acid in Algae by HPLC on Strong Cation Exchange Resin With Electrochemical Detection", *Analytical Biochemistry* 130: 191–198, (1983).

Hellman, et al., "Physiologische und biochemische Beitrage zur taxonomie der Gattungen, Ankistrodesmus und Scenedesmus. III. Die Basenzusammensetzung der DNS", *Arch. Microbiol.*, vol. 100 pp. 239–242, (1974).

Huss, et al., "Deoxyribonucleic Acid Reassociation in the Taxonomy of the Genus Chlorella, III. *Chlorella fusca* and *Chlorella kessleri*", *Arch Microbiol*, vol. 149 pp. 1–3, (1987).

Huss, et al., "Deoxyribonucleic Acid Reassociation in the Taxonomy of the Genus Chlorella, IV. *Chlorella protothecoides* and Its Relationship to the Genus Prototheca," *Arch. Microbiol* vol. 150, pp. 509–511 (1988).

Kerfin et al., "Physiological and Biochemical Contributions to the Taxonomy of the Genus Prototheca", *Arch. Microbiol*, vol. 116 pp. 105–107, (1978).

Kerfin et al., "Physiological and Biochemical Contributions to the Taxonomy of the Genus Chlorella", *Arch. Microbiol*, vol. 116, pp. 97–103, (1978).

Kessler, "Comparative Physiology and Biochemistry of Chlorella Species as the Basis for their Taxonomy and for Their Utilization in Research and Biotechnology", *Phycotalk*, vol. 1, pp. 141–153.

Kessler, "Physiological and Biochemical Contributions to the Taxonomy of the Genus Prototheca. III. Utilization of Organic Carbon and Nitrogen Compounds", *Arch. Microbiol.*, vol. 132 pp. 103–106, (1982).

Kessler, "Comparative Physiology, Biochemistry, and the Taxonomy of Chlorella (Chlorophyceae)", *Plant Syst. Evol.*, vol. 125 pp. 129–138, (1976).

Kessler et al., "Biochemical Taxonomy of Symbiotic Chlorella Strains from Paramecium and Acanthocystis", Institut fur Botanik, Universitat Erlangen–Nurnberg, Erlangen FRG, pp. 140–142, (1989).

Kessler, "Physiologische and Biochemische Beitrage zur Taxonoie der Gattung Chlorella, IX. Salzresistenc als Taxonomisches Merkmal", *Arch. Microbiol.*, vol. 100 pp. 51–56, (1974).

Kessler, "Physiological and Biochemical Contributions to the Taxonomy of the Genus Chlorella", *Arch. Microbiol*, vol. 113, pp. 139–141, (1977).

Loewus, F.A., "L–Ascorbic Acid: Metabolism, Biosynthesis, Function", *The Biochemistry of Plants*, vol. 3, pp. 77–79 (1980).

(List continued on next page.)

*Primary Examiner*—Irene Marx
*Attorney, Agent, or Firm*—Sheridan Ross P.C.

[57] ABSTRACT

The present invention is directed to methods for the production of ascorbic acid by culturing organisms of the species *C. protothecoides* and recovering ascorbic acid from the fermentation medium.

16 Claims, No Drawings

OTHER PUBLICATIONS

Maruyama, "Classification of Chlorella Strains by Cell Appearance and Group Sera", *Bot. Mag.*, Tokyo, 90, pp. 57–66, (1977).

McNamer et al., "Proline Uptake and Utilization by *Chlorella pyrenoidosa*", *Plant Physiol.* 52: 561–564, (1973).

Pore, et al., "Prototheca Ecology", *Mycopathologia* vol. 81 pp. 49–62, (1983).

Pore, "Nutritional Basis for Relating Prototheca and Chlorella," *Canadian Journal of Microbiology*, vol. 18, pp. 1175–1177 (1972).

Pore, "Prototheca Taxonomy", *Mycopathologia*, vol. 90, pp. 129–139, (1985).

Pore, "Selective Medium for the Isolation of Prototheca", *Applied Microbiology*, vol. 26, No. 4, pp. 648–649, (Oct. 1973).

Pore, "Taxonomic Status and Experimental Pathology of Prototheca Species", pp. 63–64 (1971).

Puel et al., "Etude Ultrastructurale de *Prototheca wickerhamii* (Tubaki et Soneda, 1959) Variations Observees au cours du Cycle Cellulaire", *Annales des Sciences Naturelles*, Serie 13c vol. 4, pp. 15–26, (1982).

Rehm et al., *Biotechnology*, vol. 1, pp. 297–300, (1981).

Renstrom, et al., "Biosynthesis of L–Ascorbic Acid in *Chlorella pyrenoidosa*", *Plant Science Letters*, vol. 28 pp. 299–305, (1982/83).

Shigeoka et al., "The Effect of Illumination of the L–Ascorbic Acid Content in *Euglena gracilis z*" *Agric. Biol. Chem.* 43: 2053–2058, (1979).

Shigeoka et al., "The Biosynthetic Pathway of L–Ascorbic Acid in *Euglena gracilis z*", *J. Nutr. Sci. Vitaminol* 29: 299–307, (1979).

Stanbury et al., *Principles of Fermentation Technology*, pp. 21–25, (1984).

Subbulakshmi et al., "Effect of Processing on the Nutrient Content of the Green Alga *Scenedesmus Acutus*", *Nutrition Reports International*, 14: 581–591, (1976).

Sudman, et al. "Antigenic Relationships Between Chlorella and Prototheca SPP", *Sabouraudia* vol. 12, pp. 36,4–370, (1974).

Sudman et al., Studies on the Antigenic Relationships between Prototheca and Chlorella, *Abstracts of the Annual Meeting*, Mm34 p. 141, (1974).

Takeda, "Sugar Composition of the Cell Wall and the Taxonomy of Chlorella (Chlorophyceae)", *J. Phycol.*, vol. 27, pp. 224–232, (1991).

Vaidya et al., "Secretion of a Highly Reducing Substance by Algae in Media and its Probable Role in Crop Physiology", *Science and Culture* 37: 383–384, (1971).

Vinayakumar et al., "Physiological and Biochemical Contributions to the Taxonomy of the Genus Chlorella, X. Products of Glucose Fermentation", *Arch. Microbiol*, vol. 103, pp. 13–19, (1975).

Wilcox, et al., "Assessing the Relationships of Autosporic and Zoosporic Chlorococcalean Green Algae with 18S rDNA Sequence Data", *J. Phycol.*, vol. 28, pp. 381–386 (1992).

MICROBIAL PROCESS FOR THE PRODUCTION OF ASCORBIC ACID USING *CHLORELLA PROTOTHECOIDES*

CROSS-REFERENCE TO RELATED APPLICATIONS

This application is a continuation-in-part of U.S. patent application Ser. No. 08/196,338, filed Feb. 10, 1994, now abandoned which is a continuation-in-part of U.S. patent application Ser. No. 07/853,476, filed Mar. 18, 1992, now abandoned, which is a continuation-in-part of U.S. patent application Ser. No. 07/650,886, filed Feb. 5, 1991, now abandoned, which is a continuation of U.S. patent application Ser. No. 06/750,828, filed Jul. 1, 1985, now U.S. Pat. No. 5,001,059, and a continuation-in-part of U.S. patent application Ser. No. 07/896,724, filed Jun. 9, 1992, now abandoned, which is a continuation of U.S. patent application Ser. No. 07/650,886, filed Feb. 5, 1991, now abandoned, which is a continuation of U.S. patent application Ser. No. 06/750,828, filed Jul. 1, 1985, now U.S. Pat. No. 5,001,059; and a continuation-in-part of U.S. patent application Ser. No. 07/853,379, filed Mar. 18, 1992, now abandoned, which is a continuation-in-part of U.S. patent application Ser. No. 07/650,886, filed Feb. 5, 1991, now abandoned, which is a continuation of U.S. patent application Ser. No. 06/750,828, filed Jul. 1, 1985, now U.S. Pat. No. 5,001,059, the disclosures of which are incorporated herein by reference in their entirety.

FIELD OF THE INVENTION

The present invention relates to the production of ascorbic acid by fermentation of organisms of the species *Chlorella protothecoides*, and the recovery of the ascorbic acid produced for use as a dietary supplement.

BACKGROUND OF THE INVENTION

Nearly all forms of life, both plant and animal, either synthesize ascorbic acid (e.g., Vitamin C) or require it as a nutrient. Ascorbic acid was first identified to be useful as a dietary supplement for humans and animals for the prevention of scurvy. Ascorbic acid, however, further affects human physiological functions such as the adsorption of iron, cold tolerance, the maintenance of the adrenal cortex, wound healing, the synthesis of polysaccharides and collagen, the formation of cartilage, dentine, bone and teeth, the maintenance of capillaries, and is useful as an antioxidant.

For use as a dietary supplement, ascorbic acid can be isolated from natural sources, such as rosehips, synthesized chemically through the oxidation of L-sorbose, or produced by the oxidative fermentation of calcium D-gluconate by *Acetobacter suboxidans*. Considine, "Ascorbic Acid", *Van Nostrand's Scientific Encyclopedia*, Vol. 1, pp. 237–238, (1989). It is also known to obtain predominantly intracellular L-ascorbic acid through the fermentation of microorganisms of *Chlorella pyrenoidosa*. See U.S. Pat. No. 5,001,059 by Skatrud, which is assigned to the assignee of the present application.

While production of ascorbic acid by some species of Chlorella, such as *Chlorella pyrenoidosa* has been reported, it is also recognized that the genus Chlorella is a very large and heterogenous genus, with an amazing amount of variability among the constituents. See W. Kerfin et al., "Physiological and Biochemical Contributions to the Taxonomy of the Genus Chlorella, XI. DNA Hydridization", *Arch. Microbiol.*, 116:97–103 (1978); E. Kessler, "Comparative Physiology, Biochemistry, and the Taxonomy of Chlorella (Chlorophyceae)", *Plant Syst. Evol.*, 125:129–138 (1976); E. Kessler, "Comparative Physiology and Biochemistry of Chlorella Species as the Basis for Their Taxonomy and for Their Utilization in Research and Biotechnology", *Phycotalk*, 1:141–153 (1995). In fact, researchers have suggested the reclassification of organisms species of Chlorella to no longer be in the genus Chlorella. One such microorganism is *Chlorella protothecoides*. See W. Kerf in et al., "Physiological and Biochemical Contributions to the Taxonomy of the Genus Chlorella, XI. DNA Hydridization", *Arch. Microbiol.*, 116:97–103 (1978).

The reclassification of *C. protothecoides* has been suggested due to the number of physiological, biochemical and genetic differences between *C. protothecoides* and the "typical" Chlorella. With regard to physiological differences between *C. protothecoides* and the "typical" Chlorella, one researcher has demonstrated differences in component cell wall polysaccharides of *C. protothecoides* that are not shared with other species of Chlorella. Conte et al., Taxonomic Implications of Prototheca and Chlorella Cell Wall Polysaccharide Characterization", *Arch. Mikrobiol.*, 92:227–233 (1973). Further, Conte et al. report that the monosaccharide mannose which was not detected in the cell walls of other species of Chlorella was detected in the cell walls of *C. protothecoides*, and that the monosaccharide arabinose which was not detected in the cell walls of *C. protothecoides* was found in the cell walls of other Chlorella species.

With regard to biochemical differences between *C. protothecoides* and the "typical" Chlorella, researchers have reported that *C. protothecoides*, in contrast to other species of Chlorella, is incapable of assimilating nitrate as a nitrogen source. E. Kessler, "Comparative Physiology and Biochemistry of Chlorella Species as the Basis for Their Taxonomy and for Their Utilization in Research and Biotechnology", *Phycotalk*, 1:141–153 (1995). In addition, *C. protothecoides* requires thiamine for growth, whereas other species of Chlorella do not. Ibid.; K. Maruyama, "Classification of Chlorella Strains by Cell Appearance and Group Sera", *Bot. Mag.*, 90:57–66 (1977).

With regard to genetic differences between *C. protothecoides* and "typical" Chlorella, one study has shown a low percentage of DNA hybridization (6–8%) of *C. protothecoides* with other Chlorella species. This finding led the author to suggest that a removal of *C. protothecoides* from the genus Chlorella might be necessary. See W. Kerf in et al., "Physiological and Biochemical Contributions to the Taxonomy of the Genus Chlorella, XI. DNA Hydridization", *Arch. Microbiol.*, 116:97–103 (1978).

In view of the above discussion, it should be appreciated that one skilled in the art would not have an expectation that all metabolic characteristics of one species of Chlorella are shared by all other species of Chlorella. In particular, with regard to ascorbic acid production, the fact that *Chlorella pyrenoidosa* is known to produce ascorbic acid would not lead one skilled in the art to assume that a structurally, biochemically and genetically diverse organism, such as *Chlorella protothecoides* would necessarily produce ascorbic acid. Moreover, there is a need for improved methods for producing ascorbic acid using microorganisms.

SUMMARY OF THE INVENTION

In accordance with the present invention, a process is provided for the production of L-ascorbic acid which includes culturing an organism of the species *Chlorella protothecoides* in a fermentation medium and recovering L-ascorbic acid from the fermentation medium. In a preferred embodiment of the process, the fermentation medium has a pH of less than about 6. In this manner extracellular ascorbic acid degradation in the fermentation medium is reduced and significant accumulations of ascorbic acid can be attained in the extracellular medium. Extracellular production of ascorbic acid allows for higher productivities and facilitates recovery of the product.

At least a portion of the L-ascorbic acid produced by the cultured organisms is produced extracellularly and is present in the fermentation medium. Typically, at least about 10% of the L-ascorbic acid in the fermentation medium is extracellular, but preferably at least about 25% of the L-ascorbic acid in the fermentation medium is extracellular, and more preferably at least about 50% of the L-ascorbic acid in the fermentation medium is extracellular. Such extracellular L-ascorbic acid can be recovered from the fermentation medium using a recovery process including, but not limited to, ion exchange, chromatography, extraction, solvent extraction, membrane separation, electrodialysis, reverse osmosis, distillation, chemical derivatization and crystallization.

Also in accordance with the present invention, a fermentation culture is provided which includes L-ascorbic acid-producing microalgae in a fermentation medium, wherein the fermentation medium comprises at least about 1 mg/l extracellular L-ascorbic acid and the fermentation medium has a dissolved oxygen content of at least about 20%. Such fermentation media include those having a pH of less than about 6, preferably less than about 5.5 and more preferably less than about 5. Suitable L-ascorbic acid producing microalgae include organisms of the species *Chlorella prototheocoides*.

DETAILED DESCRIPTION

The present invention is directed to the production of ascorbic acid by organisms of the species *Chlorella prototheocoides*. In particular, the present invention is directed to novel methods for producing L-ascorbic acid by culturing organisms of the species *C. prototheocoides* under a variety of culturing conditions.

The production of ascorbic acid by culturing organisms of the species *C. prototheocoides* according to the present invention provides significant advantages over known ascorbic acid production methods. One such advantage is that organisms of the species *C. prototheocoides* are acidophilic, allowing fermentation to be carried out under low pH conditions, with the fermentation medium pH typically less than about 6. Below this pH, extracellular ascorbic acid produced by *C. prototheocoides* during fermentation is relatively stable because the rate of oxidation of ascorbic acid in the fermentation medium by oxygen is reduced. Accordingly, high productivity levels can be obtained for producing L-ascorbic acid with *C. prototheocoides* according to the methods of the present invention. In addition, control of the dissolved oxygen content to very low levels to avoid oxidation of ascorbic acid is unnecessary. Moreover, this advantage allows for the use of continuous recovery methods because extracellular medium can be treated to recover the ascorbic acid product.

Another advantage of the present invention is that the organisms of the species *C. prototheocoides* have been observed to be tolerant of high levels of ascorbic acid. Desirably, a substantial amount of ascorbic acid can accumulate in the fermentation medium before the production of ascorbic acid by the microorganisms is negatively affected. As a result, ascorbic acid recovery methods are more effective and high productivity levels can be obtained for producing L-ascorbic acid with *C. prototheocoides* according to the methods of the present invention.

Yet another advantage of the present invention is that substantial quantities of L-ascorbic acid produced by *C. prototheocoides* organisms is extracellular. As demonstrated below, extracellular concentrations of ascorbic acid are about equal to total ascorbic acid concentrations, thus indicating that intracellular and extracellular concentrations are about equal. As noted above, it is substantially easier to separate extracellular L-ascorbic acid from the fermentation medium than it is to extract intracellular L-ascorbic acid from microorganisms.

A further advantage of the present invention is that the organisms of the species *C. prototheocoides* as described and used herein for producing L-ascorbic acid are heterotrophic microorganisms, and can be grown on relatively simple, inexpensive media in order to produce ascorbic acid. In addition, such organisms have been found to have relatively fast growth rates.

PRODUCTION MICROORGANISMS

Microorganisms of the species *C. prototheocoides* commonly occur in nature and can be readily obtained from various sources, such as, for example, sources described by Patrizia Albertano et al. in "*Chlorella prototheocoides* Kruger var. acidicola, a new variety from very low pH environments" *Arch. Hydrobiol. Suppl.*, 67,4:401–408, (1984), which is incorporated herein in its entirety. Organisms of the species *C. prototheocoides* have been found in low pH environments throughout Italy and Sicily, including sulfur springs, solfataras and sulfur mines. Ibid. In addition, such organisms are known to occur in tree saps. Ahmad et al., "Growth and Photosynthesis of *Chlorella Prototheocoides* under Different Nutritional Conditions" *J. Phycology*, 25, supp. 2 (1989). For example, the 1993 List of UTEX Cultures, available from the Culture Collection of Algae, Department of Botany, University of Texas at Austin, Austin, Tex. 78713-7640, lists *C. prototheocoides* strain UTEX 25 (ATCC 30407) as being isolated from the sap of wounded *Populus alba*, and *C. prototheocoides* strains UTEX 255 and UTEX 256 as being isolated from wounded elm tree sap. The large number and wide variety of reported sources indicates that these organisms are widely available throughout the natural environment.

These microorganisms can be detected and isolated from such natural sources through the use of appropriate screening techniques. Such techniques include the use of Prototheca Isolation Medium (PIM), such as is disclosed by R. S. Pore in "Selective Medium for the Isolation of Prototheca," *Appl. Microbiol.*, 26:648–649 (1973), which is incorporated herein in its entirety. PIM was developed for the isolation of Prototheca, but has been found to be useful in identifying *C. prototheocoides*. *C. prototheocoides*, however, can be readily distinguished from Prototheca because *C. prototheocoides* is photosynthetic and therefore, is green. In general, the constituents of PIM include, distilled water, potassium hydrogen phthalate about 10 g/L, sodium hydroxide about 0.9 g/L, magnesium sulfate about 0.1 g/L, potassium hydrogen phosphate about 0.2 g/L, ammonium chloride about 0.3 g/L, glucose about 10 g/L, thiamine hydrochloride about 0.001 g/L, agar about 20 g/L, and 5-fluorocytosine (5-FC) about 0.25 g/L. The medium has a pH in the range of from about 5 to about 5.2. Optionally, hexachlorocyclohexane (about 0.01 g/L before autoclaving) can be added to the PIM for control of arthropod contaminants and fumagillin bicyclohexylamine obtained from Abbott Laboratories in West Chicago, Ill. (about 0.005 g/L dissolved in ethanol and added before autoclaving) can be added to the PIM to control cyst-forming amoebae growth. It will be appreciated that components and amounts of components of PIM can be varied and the medium will still be effective to selectively isolate C. protothecoides.

The method used for isolating C. protothecoides on PIM or a variation of PIM depends on the physical characteristics of the sample. Liquid and semisolid specimens, including sediment obtained by centrifugation, are applied directly to the surface of the PIM, or diluted serially and then applied and spread with a sterile glass rod. Solid specimens, however, are chopped and blended in sterile water before plating as previously described. Alternatively, liquid samples or washings of samples such as food are filtered through 3.0 μm or 0.45 μm pore diameter filters. The filters are then pressed particulate side down on PIM and then turned particulate side up on PIM and incubated at a temperature of about 30° C. for a time period of about 48 hours. In general, incubation on PIM at about 30° C. for about 72 hours is adequate for most C. protothecoides strains. Colonies of C. protothecoides can be separated and selected using known techniques, such as smearing the cultures on agar or other suitable medium. C. protothecoides colonies thus isolated can then be selected and subcultured for use in the present invention as described in more detail below.

In addition to isolating C. protothecoides from natural sources as described above, various wild type strains are widely available from public depositories for a nominal fee. For example, the American Type Culture Collection (ATCC), located at 12301 Parklawn Drive, Rockville, Md. 20852 lists a number wild type strains of *C. protothecoides* as publicly available in their 1993 culture catalog, namely, ATCC 30407 and ATCC 30420. In addition, ATCC 75667 is now available. Typically, microorganisms deposited with public depositories such as the American Type Culture Collection are available for as long as the deposited strain is kept alive by the depository. In addition, many depositors make supplemental deposits of a deposited strain which can no longer be kept alive, thereby extending the time periods for which deposited strains are publicly available. Further, *C. protothecoides* are believed to be widely available from other depositories, such as at the Indiana Algal Culture Collection, University of Indiana and at the Algensammlung des Pflanzenphysiologischen Instituts der Universitat, Gottingen, Germany.

Although several known strains of *C. protothecoides* are mentioned herein for use in the present invention, it is within the scope of the present invention that, in addition to known strains of *C. protothecoides*, newly identified strains from nature and mutant strains derived from known or newly identified strains can be used to produce ascorbic acid. Moreover, it is recognized that taxonomic classifications of *C. protothecoides* organisms may change in the future. Therefore, the identification of known strains of *C. protothecoides* is intended to include all known *C. protothecoides* despite the fact that other strains of *C. protothecoides* have been identified in the past.

Naturally occurring mutants of a parental strain of *C. protothecoides* that are capable of producing ascorbic acid can be isolated by, for example, subjecting a parental strain to at least one round of chemical and/or radiation mutagenesis, in order to increase the rate of mutagenesis, thereby increasing the probability of obtaining a microorganism producing increased amounts of ascorbic acid. It will be obvious to one of skill in the art that mutant microorganisms of the present invention also include ascorbic acid-producing microorganisms that can be obtained by genetically engineering microorganisms to produce increased amounts of ascorbic acid. For example, it is within the purview of the present invention to transform microorganisms other than *C. protothecoides* with nucleic acid molecules encoding enzymes of the ascorbic acid biosynthetic pathway obtained from *C. protothecoides* microorganisms. A *C. protothecoides* nucleic acid molecule of the present invention can be obtained from its natural source, either as an entire (i.e., complete) genome or a portion thereof, capable of forming a stable hybrid with the entire gene. A nucleic acid molecule from a strain of *C. protothecoides* can also be reproduced using recombinant DNA technology (e.g., polymerase chain reaction (PCR) amplification, cloning) or chemical synthesis. As used herein, a "mutated microorganism" is a mutated parental microorganism in which the nucleotide composition of such microorganism has been modified by mutation(s) that occur naturally, that are the result of exposure to a mutagen, or that are the result of genetic engineering.

FERMENTATION OF *C. protothecoides*

According to the method of the present invention, L-ascorbic acid is produced by fermentation of *C. protothecoides*. In accordance with the present invention, microorganisms of the species *C. protothecoides* capable of producing L-ascorbic acid are cultured in an effective medium under effective conditions, herein defined as any medium and conditions capable of promoting L-ascorbic acid production. Preferably, the effective medium and conditions also promote rapid algal growth. In particular, the present invention provides a method to produce ascorbic acid, comprising culturing microorganisms of the species *C. protothecoides* in a medium comprising a source of assimilable organic carbon, a source of assimilable nitrogen and appropriate salts and trace metals.

Sources of assimilable carbon which can be used in a suitable fermentation medium include, but are not limited to, sugars and their polymers, including, dextrin, sucrose, maltose, lactose, glucose, fructose, mannose, sorbose, arabinose and xylose; fatty acids; organic acids such as acetate; primary alcohols such as ethanol and n-propanol; and polyalcohols such as glycerine. Preferred carbon sources in the present invention include monosaccharides, disaccharides, and trisaccharides. The most preferred carbon source is glucose.

The concentration of a carbon source, such as glucose, in the fermentation medium should promote cell growth, but not be so high as to repress growth of the microorganism used. Typically, the concentration of a carbon source, such as glucose, in the fermentation medium is greater than about 1 g/L, preferably greater than about 2 g/L, and more preferably greater than about 5 g/L. In addition, the concentration of a carbon source, such as glucose, in the fermentation medium is typically less than about 100 g/L, preferably less than about 50 g/L, and more preferably less than about 20 g/L. It should be noted that references to fermentation component concentrations can refer to both initial and/or ongoing component concentrations.

Sources of assimilable nitrogen which can be used in a suitable fermentation medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of a nitrogen source, such as anhydrous ammonia, in the fermentation medium is greater than about 0.05 g/L, preferably greater than about 0.1 g/L, and more preferably greater than about 0.15 g/L. Beyond certain concentrations, however, the addition of a nitrogen source to the fermentation medium is not advantageous for the growth of the microorganisms. As a result, the concentration of a nitrogen source, such as anhydrous ammonium, in the fermentation medium is less than about 10 g/L, preferably less than about 1 g/L and more preferably less than about 0.25 g/L. Further, in some instances it may be desirable to allow the fermentation medium to become depleted of a nitrogen source during fermentation.

The effective fermentation medium can contain other compounds such as inorganic salts, vitamins, trace metals or growth promoters. Such other compounds can also be present in carbon, nitrogen or mineral sources in the effective medium or can be added specifically to the medium.

The fermentation medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the fermentation medium is greater than about 0.5 g/L, preferably greater than about 1 g/L and more preferably greater than about 2.5 g/L. Beyond certain concentrations, however, the addition of phosphate to the fermentation medium is not advantageous for the growth of the microorganisms. Accordingly, the concentration of phosphate in the fermentation medium is typically less than about 15 g/L, preferably less than about 10 g/L and more preferably less than about 5 g/L.

A suitable fermentation medium can also include a source of magnesium, preferably in the form of a physiologically acceptable salt, such as anhydrous magnesium sulfate, although other magnesium sources in concentrations which contribute similar amounts of magnesium can be used. Typically, the concentration of magnesium in the fermentation medium is greater than about 0.001 g/L, preferably greater than about 0.003 g/L, and more preferably greater than about 0.005 g/L. Beyond certain concentrations, however, the addition of magnesium to the fermentation medium is not advantageous for the growth of the microorganisms. Accordingly, the concentration of magnesium in the fermentation medium is typically less than about 0.1 g/L, preferably less than about 0.05 g/L, and more preferably less than about 0.01 g/L. Further, in some instances it may be desirable to allow the fermentation medium to become depleted of a magnesium source during fermentation.

The fermentation medium can also include a biologically acceptable chelating agent, such as the dihydrate of trisodium citrate. In such instance, the concentration of a chelating agent in the fermentation medium is greater than about 0.2 g/L, preferably greater than about 0.5 g/L, and more preferably greater than about 1 g/L. Beyond certain concentrations, however, the addition of a chelating agent to the fermentation medium is not advantageous for the growth of the microorganisms. Accordingly, the concentration of a chelating agent in the fermentation medium is typically less than about 10 g/L, preferably less than about 5 g/L, and more preferably less than about 2 g/L.

The fermentation medium can also initially include a biologically acceptable mineral acid to neutralize excess nitrogen initially present in the fermentation medium and/or to initially control the pH of the fermentation medium. Biologically acceptable mineral acids include, but are not limited to, sulfuric acid, nitric acid, phosphoric acid and mixtures thereof. In a preferred embodiment of the present invention, the mineral acid used is sulfuric acid. Typically, the initial concentration of the mineral acid, such as 18M sulfuric acid in the fermentation medium is within the range of from about 0.05 g/L to about 15 g/L, preferably within the range of from about 0.1 g/L to about 5 g/L, and more preferably in the range of from about 0.5 g/L to about 2 g/L.

The fermentation medium can also include iron, however since it is believed iron accelerates the breakdown of extracellular L-ascorbic acid and therefore inhibits L-ascorbic acid accumulation in the medium, the amount of iron present in the fermentation medium is limited. Typically, iron (+2) is present in the fermentation medium during the initial stages of fermentation at a concentration of greater than about 0.1 mg/L, preferably at a concentration greater than about 0.3 mg/L, and more preferably at a concentration greater than about 0.7 mg/L. However, due to the tendency of excess amounts of iron to degrade ascorbic acid in the fermentation medium, iron (+2) is present in the fermentation medium at a concentration of less than about 25 mg/L, preferably at a concentration of less than about 20 mg/L, and more preferably at a concentration of less than about 15 mg/L.

The fermentation medium can also include a biologically acceptable calcium source, including, but not limited to, calcium chloride. Typically, the concentration of the calcium source, such as calcium chloride, dihydrate, in the fermentation medium is within the range of from about 5 mg/L to about 5500 mg/L, preferably within the range of from about 11 mg/L to about 1100 mg/L, and more preferably in the range of from about 55 mg/L to about 220 mg/L.

The fermentation medium can also include a biologically acceptable manganese source, including, but not limited to, manganese sulfate. Typically, the concentration of the manganese source, such as manganese sulfate, monohydrate, in the fermentation medium is within the range of from about 2 mg/L to about 1800 mg/L, preferably within the range of from about 4 mg/L to about 360 mg/L, and more preferably in the range of from about 18 mg/L to about 72 mg/L.

As previously discussed, the fermentation medium can also include a number of trace metals. Such trace metals can be added to the fermentation medium as a solution that, for convenience, can be prepared separately from the rest of the fermentation medium. A suitable trace metals solution for use in the fermentation medium is shown below in Table 1. Typically, the amount of such a trace metals solution in the fermentation medium is greater than about 1 mL/L, preferably greater than about 5 mL/L, and more preferably greater than about 10 mL/L. Beyond certain concentrations, however, the addition of a trace metals to the fermentation medium is not advantageous for the growth of the microorganisms. Accordingly, the amount of such a trace metals solution in the fermentation medium is typically less than about 100 mL/L, preferably less than about 50 mL/L, and more preferably less than about 30 mL/L. It should be noted that, in addition to adding trace metals in a solution, the individual components can be added separately, each within ranges corresponding independently to the amounts of the components dictated by the above ranges of the trace metals solution.

As shown below in Table 1, a suitable trace metals solution for use in the present invention can include cobalt (II) chloride, pentahydrate; boric acid; zinc (II) sulfate, heptahydrate; sodium molybdate, dihydrate; vanadyl sulfate, dihydrate; nickel (II) nitrate, hexahydrate; and sodium selenite.

TABLE 1

TRACE METALS SOLUTION

| COMPOUND | CONCENTRATION OF METAL (mg/L) |
|---|---|
| Cobalt (II) chloride, pentahydrate | 40 |
| Boric acid | 160 |
| Zinc (II) sulfate, heptahydrate | 400 |
| Sodium molybdate, dihydrate | 19 |
| Vanadyl sulfate, dihydrate | 20 |
| Nickel (II) nitrate, hexahydrate | 8 |
| Sodium selenite | 16 |

The microorganisms of the species *C. protothecoides* of the present invention can be cultured in conventional fermentation modes, which include, but are not limited to, batch, fed-batch, and continuous. It is preferred, however, that the fermentation be carried out in fed-batch mode. In such a case, during fermentation some of the components of the medium are depleted. It is possible to initiate fermentation with relatively high concentrations of such components so that growth is supported for a period of time before additions are required. The preferred ranges of these components are maintained throughout the fermentation by making additions as levels are depleted by fermentation. Levels of components in the fermentation medium can be monitored by, for example, sampling the fermentation medium periodically and assaying for concentrations. Alternatively, once a standard fermentation procedure is developed, additions can be made at timed intervals corresponding to known levels at particular times throughout the fermentation. As will be recognized by those in the art, the rate of consumption of nutrient increases during fermentation as the cell density of the medium increases. Moreover, to avoid introduction of foreign microorganisms into the fermentation medium addition is performed using aseptic addition methods, as are known in the art. In addition, a small amount of anti-foaming agent may be added during the fermentation.

The temperature of the fermentation medium can be any temperature suitable for growth and ascorbic acid production. For example, prior to inoculation of the fermentation medium with an inoculum, the fermentation medium can be brought to and maintained at a temperature in the range of from about 20° C. to about 45° C., preferably to a temperature in the range of from about 25° C. to about 400° C., and more preferably in the range of from about 30° C. to about 38° C.

As noted above, a significant advantage of the present invention is that *C. protothecoides* are acidophilic organisms, and thus, the present process can be conducted at low pH. The benefit of this process is that at low pH, extracellular ascorbic acid produced by the organism is degraded at a reduced rate than if the fermentation medium was at higher pH. For example, prior to inoculation of the fermentation medium with an inoculum, the pH of the fermentation medium can be adjusted, and further monitored during fermentation. Typically, the pH of the fermentation medium is brought to and maintained below about 6, preferably below 5.5, and more preferably below about 5. The pH of the fermentation medium can be controlled by the addition of ammonia or acid to the fermentation medium. In such cases when ammonia is used to control pH, it also conveniently serves as a nitrogen source in the fermentation medium.

The fermentation medium can also be maintained to have a dissolved oxygen content during the course of fermentation to maintain cell growth and to maintain cell metabolism for L-ascorbic acid formation. The oxygen concentration of the fermentation medium can be monitored using known methods, such as through the use of an oxygen probe electrode. Oxygen can be added to the fermentation medium using methods known in the art, for example, through agitation and aeration of the medium by stirring or shaking. Preferably, the oxygen concentration in the fermentation medium is in the range of from about 20% to about 100% of the saturation value of oxygen in the medium based upon the solubility of oxygen in the fermentation medium at atmospheric pressure and at a temperature in the range of from about 30° C. to about 40° C. Periodic drops in the oxygen concentration below this range may occur during fermentation, however, without adversely affecting the fermentation.

Although aeration of the medium has been described herein in relation to the use of air, other sources of oxygen can be used. Particularly useful is the use of an aerating gas which contains a volume fraction of oxygen greater than the volume fraction of oxygen in ambient air. In addition, such aerating gases can include other gases which do not negatively affect the fermentation.

In an embodiment of the fermentation process of the present invention, a fermentation medium is prepared as described above. This fermentation medium is inoculated with an actively growing culture of microorganisms of the species *C. protothecoides* in an amount sufficient to produce, after a reasonable growth period, a high cell density. Typical inoculation cell densities are within the range of from about 0.1 g/L to about 15 g/L, preferably from about 0.5 g/L to about 10 g/L and more preferably from about 1 g/L to about 5 g/L, based on the dry weight of the cells. The cells are then grown to a cell density in the range of from about 10 g/L to about 100 g/L preferably from about 20 g/L to about 80 g/L, and more preferably from about 50 g/L to about 70 g/L. The residence times for the microorganisms to reach the desired cell densities during fermentation are typically less than about 200 hours, preferably less than about 120 hours, and more preferably less than about 96 hours.

In one mode of operation of the present invention, the carbon source concentration, such as the glucose concentration, of the fermentation medium is monitored during fermentation. Glucose concentration of the fermentation medium can be monitored using known techniques, such as, for example, use of the glucose oxidase enzyme test or high pressure liquid chromatography, which can be used to monitor glucose concentration in the supernatant, e.g., a cell-free component of the fermentation medium. As stated previously, the carbon source concentration should be kept below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose concentration in the fermentation medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is preferred to maintain the carbon source concentration of the fermentation medium by addition of aliquots of the original fermentation medium. The use of aliquots of the original fermentation medium are desirable because the concentrations of other nutrients in the medium (e.g. the nitrogen and phosphate sources) can be maintained simultaneously. Likewise, the trace metals concentrations can be maintained in the fermentation medium by addition of aliquots of the trace metals solution.

A further novel aspect of the present invention is a fermentation culture which L-ascorbic acid-producing microalgae and a fermentation medium, wherein the fermentation medium comprises at least about 1 mg/l extracellular L-ascorbic acid and a dissolved oxygen content of at least about 20% saturation. The fermentation culture preferably comprises organisms of the genus Prototheca. Preferably, the pH of said fermentation medium is less than about 6, more preferably less than about 5.5 and most preferably less than about 5.

As stated previously, the present invention provides significant advantages for the production of ascorbic acid. In particular, the organisms of the species *C. protothecoides* as described and used herein produce significant quantities of extracellular L-ascorbic acid. Extracellular L-ascorbic acid can be recovered from the fermentation medium using conventional separation and purification techniques. For example, the fermentation medium can be filtered or centrifuged to remove microorganisms, cell debris and other particulate matter, and L-ascorbic acid can be recovered from the cell-free supernate by conventional methods, such as, for example, ion exchange, chromatography, extraction, solvent extraction, membrane separation, electrodialysis, reverse osmosis, distillation, chemical derivatization and crystallization.

One such example of L-ascorbic acid recovery is provided in U.S. Pat. No. 4,595,659 by Cayle, incorporated herein in its entirety be reference, which discloses the isolation of L-ascorbic acid from an aqueous fermentation medium by ion exchange resin adsorption and elution, which is followed by decoloration, evaporation and crystallization. Further, isolation of the structurally similar isoascorbic acid from fermentation medium by a continuous multi-bed extraction system of anion-exchange resins is described by K. Shimizu, *Agr. Biol. Chem.* 31:346–353 (1967), which is incorporated herein in its entirety by reference.

Intracellular L-ascorbic acid produced in accordance with the present invention can also be recovered and used in a variety of applications. For example, *C. protothecoides* cells can be lysed and the ascorbic acid which is released can be recovered by a variety of known techniques. Alternatively, intracellular ascorbic acid can be recovered by washing the cells to extract the ascorbic acid, such as through diafiltration.

In a further aspect of the present invention, intracellular ascorbic acid is recovered by combining microorganisms of the species *C. protothecoides* with food material to enhance the ascorbic acid content of such food material. As used herein, the phrase "food product" refers to any food type fed to humans or non-human animals, including human food and animal feed, with animal feed being preferred. Such animal feed includes, but is not limited to, feed for poultry, swine, horses, cattle and fish. Preferred animal feed can include, meat meal, fish meal, corn, corn gluten meal, soybean meal, silage, brewer's grains, hay, alfalfa hay, alfalfa meal, oats, barley, wheat, wheat bran, sorghum, canola meal, rice bran polishings, whole cottonseed and cottonseed meal.

In the embodiment of a food product being an animal food product, the amount of microorganisms typically added to the food product is within the range of from about 0.1% by weight (wt %) and about 5 wt %, more preferably within the range of from about 0.2 wt % and about 2 wt %, and most preferably within the range of from about 0.5 wt % and about 1 wt %. Such food products typically have an ascorbic acid content within the range of from about 0.001 wt % and about 0.25 wt %, more preferably within the range of from about 0.005 wt % and about 0.15 wt %, and most preferably within the range of from about 0.01 wt % and about 0.05 wt %.

The following experimental results are provided for the purposes of illustration and are not intended to limit the scope of the invention. References to "UTEX" strains in the following Examples refers to *C. protothecoides* strains obtained form the Culture Collection of Algae, Department of Botany, University of Texas at Austin, Austin, Tex. 78713-7640.

EXAMPLES

EXAMPLE 1

The following example illustrates the production of L-ascorbic acid by microorganisms of the species *C. protothecoides*.

Fermentation Medium Preparation

Trace Metals Solution

The compounds listed in Table 2 and 20 mL of concentrated hydrochloric acid were made up to 1 L with distilled water.

TABLE 2

TRACE METALS SOLUTION

| COMPOUND | CONCENTRATION OF METAL (mg/L) |
|---|---|
| Calcium chloride, dihydrate | 3102 |
| Manganese (II) sulfate, monohydrate | 400 |
| Copper (II) sulfate, monohydrate | 16 |
| Cobalt (II) chloride, pentahydrate | 40 |
| Boric acid | 160 |
| Zinc (II) sulfate, heptahydrate | 400 |
| Sodium molybdate, dihydrate | 19 |
| vanadyl sulfate, dihydrate | 20 |
| Nickel (II) nitrate, hexahydrate | 8 |
| Sodium selenite | 16 |

Glucose-Salts Medium

The various compounds listed in Table 3 were heat sterilized and combined in a flask after cooling to a final volume of 600 mL.

TABLE 3

Glucose-Salts Medium

| Amount | Compound |
|---|---|
| 56 g | Glucose, food grade monohydrate (anhydrous basis) in 80 mL water |
| 0.7 g | Trisodium citrate dihydrate |
| 0.46 g | Magnesium sulfate, anhydrous |
| 0.7 mL | Sulfuric acid in 10 mL water |
| 0.65 g | Monobasic sodium phosphate |
| 1.3 g | Monobasic potassium phosphate |
| 0.68 g | Dibasic sodium phosphate in 10 mL water |
| 9.4 mL | Trace Metals Solution (shown above in Table 2) |

Phosphate Medium

A solution containing 0.27 g monobasic potassium phosphate and 0.23 g dibasic sodium phosphate dissolved in 600 mL distilled water was heat-sterilized in a 1 L glass fermentor. After the medium had cooled, 5 mL of a 1.9 g/L ferrous sulfate heptahydrate solution was added through a sterile filter having a pore size of 0.2 µm.

A 20 mL sample of the Glucose-Salts Medium was added to the Phosphate Medium in the fermentor to form a fermentation medium. The glass fermentor was equipped with an apparatus for agitating the medium and an apparatus for adding oxygen and nutrient components during fermentation.

Cell Growth and L-Ascorbic Acid Production

The fermentation medium was heated and the temperature was maintained at 35° C. Agitation of the fermentation medium began at 300 rpm. Air was sparged into the medium at 0.1 L/min, and the pH of the medium was adjusted to 6.9 with ammonia which was added to the airflow. The fermentation medium was inoculated with an actively growing culture of *C. protothecoides*, BTR 902 (ATCC 75667), to give an initial cell density of approximately 0.3 g/L by dry weight of the cells.

The cells were grown in the fermentor at a growth rate of 0.16 h$^{-1}$ to a cell density of about 37 g/L by dry weight of the cells. For the first 18 hours of the fermentation, the pH of the fermentation medium was maintained at about pH 5 by the addition of gaseous ammonia into the airflow. The addition of ammonia was then stopped, and the pH of the fermentation medium was allowed to drop to about pH 3.5. The pH of the fermentation medium was then maintained at 3.5 by the addition of gaseous ammonia for the remainder of the fermentation. To maintain dissolved oxygen in the range of from about 20% to about 90% of the saturation value during the course of the fermentation, agitation of the fermentation medium was gradually increased to 700 rpm.

Glucose concentration in the fermentation medium was monitored either by the glucose oxidase enzyme test or by high pressure liquid chromatography by taking a cell-free (supernate) sample of the fermentation medium. When the glucose concentration of the fermentation medium dropped below the original concentration level, it was replenished by adding 20% aliquots of the previously prepared Glucose-Salts Medium to the fermentor, while keeping the total glucose concentration of the fermentation medium below 30 g/L. After the entire prepared amount of Glucose-Salts Medium had been added, the fermentation medium was assayed for L-ascorbic acid.

L-Ascorbic Acid Assay

The method used for quantifying L-ascorbic acid is described by Grun and Loewus, *Analytical Biochemistry*, 130:191–198, (1983). The method is an ion-exchange procedure, using a 7.8×300 mm organic acid analysis column, HPX-87, obtained from Bio-Rad Laboratories in Richmond, Calif. The assay conditions were: mobile phase, 0.013M nitric acid; flow rate 0.8 mL/min; pressure 1500 psig; detection, absorbance at 245 nm. The total L-ascorbic acid (Total L-AA) in the fermentation medium was determined by assaying for ascorbic acid in the fermentation supernatant and for ascorbic acid extracted from the cells by contacting the cells with 2.5% trichloroacetic acid (TCA) for about 10 minutes.

Cell Density Determinations

For dry weight determinations of cell density, 5 mL whole medium samples were removed from the fermentor and centrifuged at 4000×g for 5 minutes, and the pellet obtained was washed once with distilled water, and then washed into a tared aluminum weighing dish. Cells were dried for a period of time in the range of from about 8 hours to about 24 hours at 60° C., and for an additional hour at 105° C. The dry weight of the cells was calculated by difference. Results expressed as an average of the four fermentations are given below in Table 4.

TABLE 4

| Time (hr) | pH | Dry Cell Weight (g/L) | Total L-AA (mg/L) | Supernatant L-AA (mg/L) | Comments |
|---|---|---|---|---|---|
| 5 | 5.1 | 0.6 | | | 300 rpm; 50 mL* |
| 18 | 5 | 4.8 | | | |
| 22 | | | | | 400 rpm; 350 mL* |
| 24 | 3.4 | 11.9 | 15.2 | 1.8 | 600 mL; 4 L/min |
| 27 | 3.4 | 17 | 24.5 | 11.2 | 700 rpm$^b$ |
| 32 | 3.5 | 23.5 | 64 | 21 | |
| 35 | 3.5 | 36.7 | 100.4 | 52 | Glucose Depleted |

*Glucose-Salts Medium.
$^b$1800 mL of Glucose-Salts Medium added over the next 3 hr.

As shown in Table 4 above, a significant amount of extracellular L-ascorbic acid was measured in the fermentation medium, even with measurable dissolved oxygen in the fermentation medium.

EXAMPLE 2

The following example further illustrates the production of ascorbic acid using known strains of *C. protothecoides*.

Fermentation Medium Preparation

The fermentation medium used for the strains contained potassium phosphate monobasic 0.82 g/L, potassium phosphate dibasic 4.2 g/L, trisodium citrate 7.7 g/L, magnesium sulfate 0.6 g/L, ammonium sulfate 3.5 g/L, trace metals solution (as described previously in Table 2) of 2 mL/L, yeast extract 2.5 g/L, glucose 30 g/L, and thiamine HCl 1 mg/L. The growth medium had a starting pH of about 7.

Cell Growth and L-Ascorbic Acid Production

A total of 9 wild type strains of *C. protothecoides* were cultured under the following conditions. Cells of each strain were inoculated into 50 mL of the previously prepared fermentation medium in 250 mL baffled Erlenmeyer flasks and incubated at 30° C. while being agitated at 160 rpm.

When optical density readings indicated that cell density was high enough for accurate ascorbic acid assay, whole medium samples were withdrawn for analysis. For the ascorbic acid assay, 2.0 mL samples of whole medium were combined with 250 µL of 25% trichloroacetic acid, mixed, and allowed to stand 15 minutes to extract. This whole medium extract was centrifuged to pellet the cells and the supernate was assayed for ascorbic acid. The ascorbic acid standards were prepared from 10,000 mg/L ascorbic acid stock solution in 5% trichloroacetic acid. The reaction mixture was prepared by 250 µL of whole medium extract (or ascorbic acid standard for baseline), 100 µL of o-phosphoric acid, and 2 mL of color reagent. The color reagent used was prepared by combining four parts of 0.5% 2,2'-dipyridyl with one part 8.3 mM ferric ammonium sulfate. The mixture was allowed to stand one hour at room temperature, and its absorbance was read at 525 nm. Ascorbic acid concentrations were calculated based on observances of the ascorbic acid standards.

For dry weight determinations, 5 mL of each culture was centrifuged to pellet cells, the supernates were decanted, and cells were resuspended in 5 mL of distilled water and recentrifuged. Supernates were again decanted, and the washed cells were washed into tared aluminum weighing dishes. Cells were dried at 60° C. overnight and 105° C. for an additional two hours. Pans with dried cells were cooled in a desiccator and weighed. Cell dry weights were calculated by difference.

The results of these experiments, as shown below in Table 5, clearly indicate that all 9 wild type strains tested of *C. protothecoides* produced ascorbic acid.

TABLE 5

ASCORBIC ACID PRODUCTION BY
*C. PROTOTHECOIDES* STRAINS

| C. protothecoides Strain | L-Ascorbic Acid (mg) per gram of dry cell weight | Growth rate, h$^{-1}$ |
|---|---|---|
| ATCC 75667 | 1.2 | 0.17 |
| UTEX 249 | 1.2 | 0.144 |
| UTEX 25* | 1.2 | 0.086 |
| UTEX 411 | 1 | 0.087 |
| UTEX 29 | 0.64 | 0.08 |
| UTEX 250 | 0.82 | 0.04 |
| UTEX 256 | 0.56 | 0.052 |
| UTEX 31 | 0.46 | 0.058 |
| UTEX 255 | 0.5 | 0.027 |

*ATCC 30407

ATCC No. 75667, identified as *Chlorella protothecoides* RSP902 (unicellular green microalga), was deposited on Feb. 8, 1994, with the American Type Culture Collection (ATCC), Rockville, Md., 20852, USA, under the terms of the Budapest Treaty on the International Recognition of the Deposit of Microorganisms for the Purpose of Patent Procedure.

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. A process for the production of L-ascorbic acid, the process comprising the steps of:
   (a) culturing an organism of the species *C. protothecoides* in a fermentation medium containing assimilable sources of carbon and nitrogen; and
   (b) recovering L-ascorbic acid from said fermentation medium.

2. The process claimed in claim 1, wherein said fermentation medium has a pH of less than about 6.

3. The process claimed in claim 1, wherein said fermentation medium has a pH of less than about 5.5.

4. The process claimed in claim 1, wherein said fermentation medium has a pH of less than about 5.

5. The process claimed in claim 1, wherein said organism of the species *C. protothecoides* produces extracellular L-ascorbic acid, and extracellular L-ascorbic acid accumulates in said fermentation medium.

6. The process claimed in claim 1, wherein said step of recovering L-ascorbic acid from said fermentation medium comprises recovering extracellular L-ascorbic acid from said fermentation medium.

7. The process claimed in claim 6, wherein said step of recovering L-ascorbic acid from said fermentation medium comprises a process selected from the group consisting of ion exchange, chromatography, extraction, solvent extraction, electrodialysis, membrane separation, reverse osmosis, distillation, chemical derivatization and crystallization.

8. The process claimed in claim 1, wherein said step of recovering further comprises the step of recovering intracellular L-ascorbic acid.

9. The process claimed in claim 1, wherein at least about 10% of said L-ascorbic acid in said fermentation medium is extracellular.

10. The process claimed in claim 1, wherein at least about 25% of said L-ascorbic acid in said fermentation medium is extracellular.

11. The process claimed in claim 1, wherein at least about 50% of said L-ascorbic acid in said fermentation medium is extracellular.

12. The process claimed in claim 1, wherein the cell density of said organism in said fermentation medium is within the range of from about 10 g/l to about 100 g/L.

13. A process for the production of L-ascorbic acid, the process comprising the steps of:
   (a) culturing an organism of the species *C. protothecoides* in a fermentation medium having a pH of less than about 6 and an available source of oxygen until said fermentation medium has a concentration of extracellular L-ascorbic acid of greater than about 1 mg/l; and
   (b) recovering extracellular L-ascorbic acid from said fermentation medium.

14. The process claimed in claim 13, wherein said step of recovering extracellular L-ascorbic acid from said fermentation medium comprises a process selected from the group consisting of ion exchange, chromatography, extraction, solvent extraction, electrodialysis, membrane separation, reverse osmosis, distillation, chemical derivatization and crystallization.

15. The process claimed in claim 13, wherein said fermentation medium has a pH of less than about 5.5.

16. The process claimed in claim 13, wherein said fermentation medium has a pH of less than about 5.

* * * * *